(12) United States Patent
Amoah

(10) Patent No.: US 7,377,918 B2
(45) Date of Patent: May 27, 2008

(54) ELECTROSURGICAL METHOD AND APPARATUS

(75) Inventor: Francis Amoah, Cardiff (GB)

(73) Assignee: Gyrus Medical Limited, Cardiff (GB)

( * ) Notice: Subject to any disclaimer, the term of this patent is extended or adjusted under 35 U.S.C. 154(b) by 301 days.

(21) Appl. No.: 11/109,778

(22) Filed: Apr. 20, 2005

(65) Prior Publication Data

US 2005/0251128 A1    Nov. 10, 2005

Related U.S. Application Data

(60) Provisional application No. 60/578,873, filed on Jun. 14, 2004.

(30) Foreign Application Priority Data

Apr. 28, 2004   (GB)   ............... 0409483.5

(51) Int. Cl.
*A61B 18/04* (2006.01)
(52) U.S. Cl. ............... 606/34; 606/32; 606/41; 606/42
(58) Field of Classification Search .......... 606/31, 606/34, 41, 42; 607/101–102
See application file for complete search history.

(56) References Cited

U.S. PATENT DOCUMENTS

| 4,411,266 | A | * | 10/1983 | Cosman | 606/49 |
|---|---|---|---|---|---|
| 5,421,819 | A | * | 6/1995 | Edwards et al. | 604/22 |
| 5,456,682 | A | * | 10/1995 | Edwards et al. | 606/31 |
| 5,549,644 | A | * | 8/1996 | Lundquist et al. | 604/22 |
| 5,843,021 | A | * | 12/1998 | Edwards et al. | 604/22 |
| 5,906,614 | A | * | 5/1999 | Stern et al. | 606/42 |
| 6,056,745 | A | * | 5/2000 | Panescu et al. | 606/42 |
| 6,126,657 | A | * | 10/2000 | Edwards et al. | 606/45 |
| 6,293,943 | B1 | * | 9/2001 | Panescu et al. | 606/41 |
| 6,500,172 | B1 | * | 12/2002 | Panescu et al. | 606/31 |
| 6,577,902 | B1 | * | 6/2003 | Laufer et al. | 607/102 |
| 2003/0055419 | A1 | * | 3/2003 | Panescu et al. | 606/34 |
| 2003/0065322 | A1 | * | 4/2003 | Panescu et al. | 606/41 |
| 2003/0073989 | A1 | * | 4/2003 | Hoey et al. | 606/34 |

FOREIGN PATENT DOCUMENTS

DE    3838840 A1    5/1990

* cited by examiner

*Primary Examiner*—Michael Peffley
*Assistant Examiner*—Victoria W Chen
(74) *Attorney, Agent, or Firm*—Oliff & Berridge, PLC

(57) ABSTRACT

Apparatus for forming a lesion in body tissue includes a probe having an active region with an electrode for contacting tissue to be treated, and an inactive region including an insulative sleeve around a portion of the electrode. The temperature of the inactive region is monitored using a temperature sensor. A controller supplies radio frequency energy to the electrode and samples signals from the temperature sensor. By performing a calculation using the sampled signals and a predetermined inactive region threshold temperature, and by adjusting the supplied radio frequency power, the inactive region of the probe can be maintained at or below an inactive region maximum temperature while the controller continues to supply radio frequency energy to the electrode. The probe has a second temperature sensor, mounted at a distal end of the electrode, the controller being configured to reduce the supplied radio frequency power when the electrode temperature reaches a predetermined maximum electrode temperature.

4 Claims, 3 Drawing Sheets

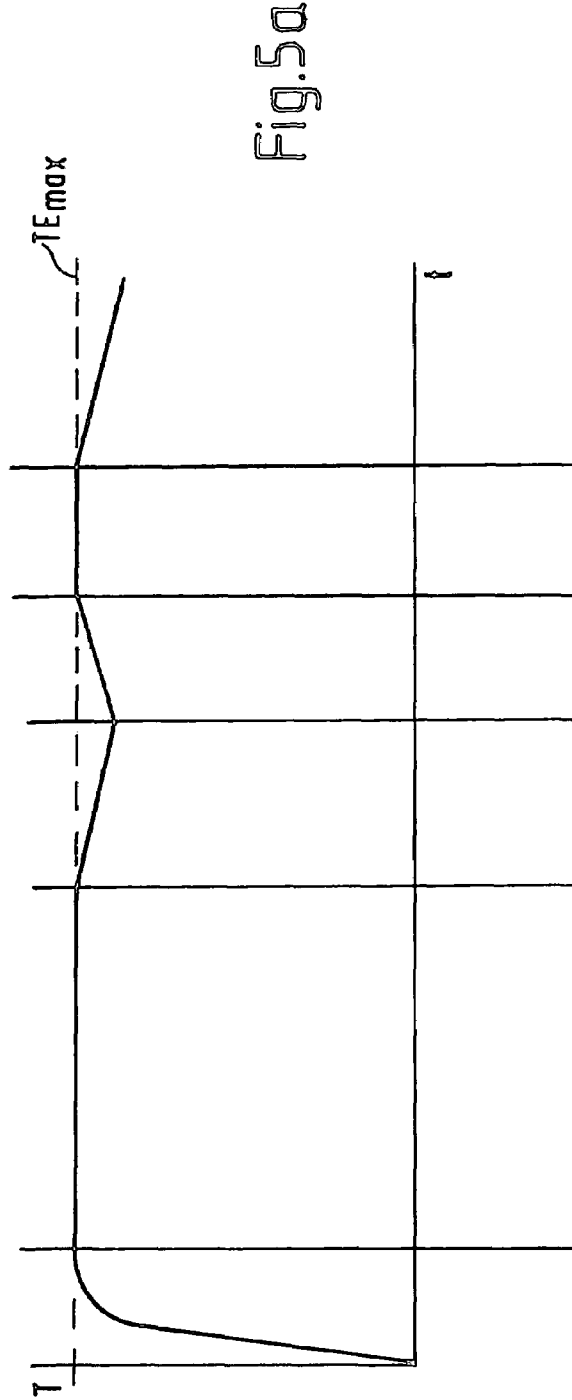
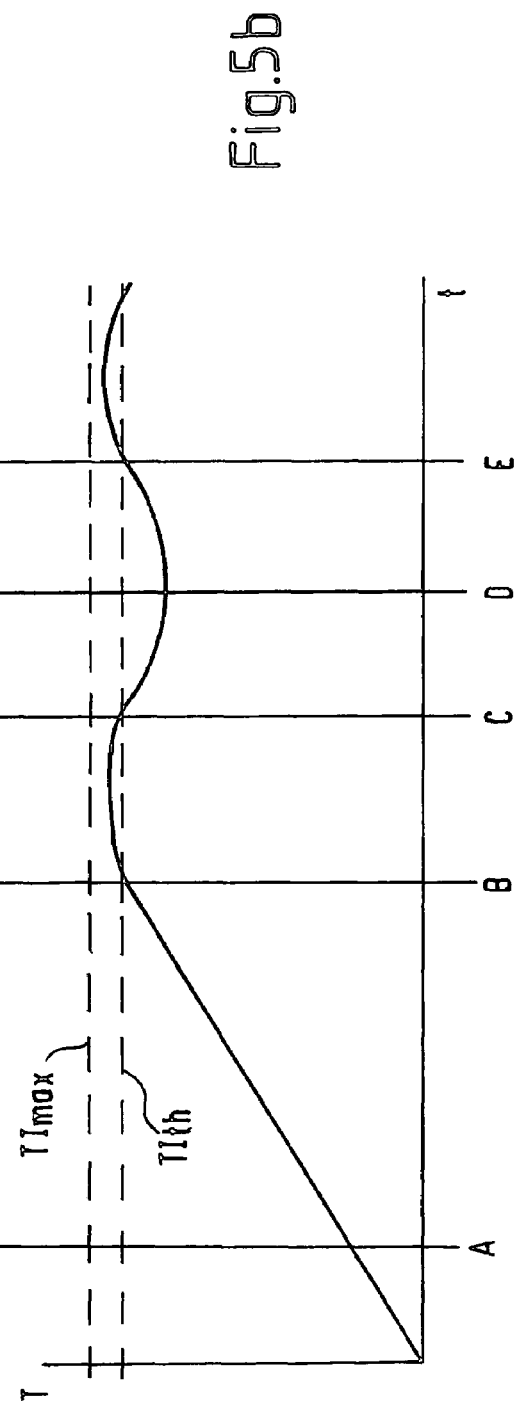

ELECTROSURGICAL METHOD AND APPARATUS

This nonprovisional application claims the benefit of U.S. Provisional Application No. 60/578,873, filed Jun. 14, 2004.

FIELD OF THE INVENTION

This invention relates to an electrosurgical system comprising an electrosurgical generator and a handpiece including electrosurgical electrodes. In particular, this invention is directed to electrosurgical systems capable of forming a lesion in body tissue, as is known for the treatment of various medical conditions including airway obstructions and sleep apnea.

BACKGROUND OF THE INVENTION

It is well known in the field of electrosurgery that there are two distinct tissue effects which can be achieved using radio frequency (RF) energy, depending on the temperature to which the tissue is raised. The first is the removal of tissue by vaporisation, in which the electrode or electrodes are subjected to relatively high temperatures (typically over 1000° C.). The second is the production of tissue necrosis without the removal of tissue in situ, and it is to this second type of system to which the present invention is directed.

U.S. Pat. No. 5,843,021 discloses a typical example of this type of treatment, in which a probe including a tissue treatment electrode is placed in contact with body tissue, and an RF signal is supplied to the probe such that the electrode heats the tissue causing cell necrosis and forming a lesion. The lesion is subsequently absorbed by the body with the result that tissue shrinkage is seen to occur. This type of treatment has been successfully performed for a number of years, and is known as "Somnoplasty".

It is well known that to produce a lesion the temperature of the tissue should be kept below 100° C. Temperatures above 100° C. are known to cause charring and desiccation of the tissue (which can be undesirable as the desiccated tissue is unable to absorb any further RF energy). The prior art teaches that temperatures in the range of 80° C. to 100° C. are typical for this type of apparatus. Examples of prior art patents teaching temperatures in this range are U.S. Pat. No. 6,126,657, U.S. Pat. No. 4,411,266, U.S. Pat. No. 5,549,644, U.S. Pat. No. 5,456,682 and U.S. Pat. No. 6,056,745. As can be seen from these and any many other prior art documents, the instruction to maintain the temperature below 100° C. is well established. For example in U.S. Pat. No. 4,411,266 it is stated "any non-uniform hot spots must be monitored to prevent runaway flash heating to the boiling point of 100° C." U.S. Pat. No. 6,056,745 states "The maximum temperature condition T.sub.MAX lies within a range of temperatures which are high enough to provide deep and wide lesions (typically between about 90° C. and 98° C.), but which are safely below about 100° C., at which tissue desiccation or tissue boiling is known to occur." As can be seen, the direction to maintain the probe temperature below 100° C. is seen as an essential requirement for successful lesion generation.

The problem with this requirement to maintain the probe temperature below 100° C. is that this can lead to a relatively slow process, requiring anything up to several minutes of treatment time in order to generate the lesion. Unless the control of the energy delivered to the probe is exceptional, the safest way to ensure that the probe temperature does not under any circumstances exceed 100° C. is to drive the device such that its normal operating is well below 100° C. Many devices operate at temperatures of between 80° C. and 85° C. (see U.S. Pat. No. 4,411,266 for example), which can lead to even longer treatment times.

Another reason that many prior art lesion generation devices operate at relatively lower temperatures is the concern that the insulation covering the probe electrode will heat up to an unacceptable extent. Even though the insulation is often set back from the tip of the electrode, any attempt to drive the probe at a level capable of causing relatively fast lesion generation runs the risk that the temperature of the insulation will rise also. If the insulation rises to a temperature at which it, in addition to the electrode, is capable of causing tissue-altering effects, tissue which is not intended to be altered may become affected. It is for this reason that some existing lesion-generating devices measure the temperature of the insulation and cause power to the device to be disconnected if the insulation temperature reaches a predetermined cut-out temperature.

The problem with this type of cut-out arrangement is that, although it does guard against inadvertent tissue damage, the cut-out feature may be frequently triggered. This leads the users and designers of such equipment to operate it at much lower power levels so as to ensure that the equipment operates well under the temperatures needed to cause a cut-out. The result is once again a relatively slow lesion. The present invention seeks to provide a lesion generation system which can produce effective lesions using considerably reduced treatment times, while attempting to mitigate the risk of insulation overheating and consequent tissue damage.

SUMMARY OF THE INVENTION

Accordingly there is provided apparatus for forming a lesion in body tissue, the apparatus comprising;
i) a probe adapted to contact body tissue, and having an active region including at least one electrode, and an inactive region including an insulative member covering at least a portion of the electrode,
ii) at least one temperature sensor capable of measuring the temperature of the inactive region and generating signals representative of the said temperature,
iii) a controller comprising,
   a) generation means for generating electromagnetic energy and supplying the said energy to the at least one electrode, and
   b) control means for receiving the signals from the temperature sensor and for controlling the generation means, the control means being capable of sampling the signals representing the inactive region temperature, performing a calculation using the sampled signals and an electrode threshold temperature, and adjusting the generation means so as to continue to supply electromagnetic energy to the electrode but at a different power, so as to maintain the inactive region at or below an inactive region maximum temperature.

The control means is adapted to control the generation means such that the temperature of the inactive region is never allowed to exceed the maximum level. There will, inevitably, be a time lag between the reduction in the power supplied to the electrode and a corresponding reduction in the temperature of the inactive region. For this reason the inactive region threshold temperature is slightly lower than the inactive region maximum temperature. The inactive region threshold temperature is preferably between 45° C. and 65° C., and is typically 62° C. The inactive region maximum temperature is preferably 65° C., the temperature at which tissue adjacent the inactive region will be rendered non-viable.

The control means is conveniently adapted to compare the inactive region temperature and the inactive region threshold temperature. In an alternative arrangement, the control means is adapted to calculate an extrapolated forecast of the inactive region temperature after a preset period of time, and compare the forecast with the inactive region threshold temperature. For example, the control means may calculate the rate of change of the temperature from a series of readings, and take action to adjust the power of the electromagnetic energy supplied by the generation means if it appears that the temperature is likely to exceed the threshold within a few seconds. In this way the apparatus is capable of responding in advance of the temperature threshold being breached, and can compensate for any delay between the power being altered and the change in power starting to take effect.

The apparatus preferably also includes at least one further temperature sensor capable of measuring the temperature of the electrode and generating further signals in response thereto. The control means is conveniently capable of sampling the further signals representing the electrode temperature, performing a similar calculation using the sampled signals and an electrode threshold temperature, and adjusting the generation means so as to maintain the electrode temperature at the electrode threshold temperature. As before, the calculation can be a simple direct comparison between the measured temperature and the threshold, or an extrapolation based on prior measurements. The electrode threshold temperature is preferably between 105° C. and 115° C., and is typically substantially 110° C.

The invention also resides in a method of forming a lesion in body tissue comprising the steps of
i) providing a probe capable of contacting body tissue to be treated, the probe having an active region including at least one electrode and an inactive region including an insulative member covering at least a portion of the electrode,
ii) delivering electromagnetic energy to the probe such as to raise the temperature of the tissue in contact with the probe,
iii) measuring the temperature of the inactive region,
iv) undertaking a calculation using the measured temperature and a predetermined inactive region threshold temperature, and
v) continuing to supply electromagnetic energy, but at different power levels depending on the result of the calculation, such that the inactive region is maintained at or below an inactive region maximum temperature.

As stated previously, the calculation conceivably comprises comparing the measured temperature with the predetermined inactive region threshold temperature. Alternatively, the calculation comprises determining, from the measured temperature and the rate of change of the measured temperature, whether the extrapolated forecast of the measured temperature will be greater than the inactive region threshold temperature within a preset period of time. The inactive region threshold temperature is conveniently between 45° C. and 65° C., and typically substantially 62° C. As before, the inactive region maximum temperature is preferably 65° C.

The method preferably also includes the additional step of measuring the temperature of the electrode, and conveniently controlling the delivery of the electromagnetic energy such that the electrode is maintained at a predetermined electrode threshold temperature. The electrode threshold temperature is preferably between 105° C. and 115° C., and typically substantially 110° C.

The invention further resides in a method of forming a lesion in body tissue comprising the steps of
i) providing a probe capable of contacting body tissue to be treated, the probe comprising at least one electrode and an insulative member covering at least a portion of the electrode,
ii) delivering electromagnetic energy to the probe such as to raise the temperature of the tissue in contact with the probe,
iii) measuring the temperature of the electrode,
iv) comparing the temperature of the electrode with a predetermined electrode target temperature,
v) increasing the delivery of the electromagnetic energy until the electrode reaches the predetermined electrode target temperature,
vi) controlling the delivery of the electromagnetic energy such that the electrode is maintained at the predetermined electrode target temperature,
vii) measuring the temperature of the insulative member,
viii) comparing the temperature of the insulative member with a predetermined insulation threshold temperature, and
ix) adjusting the electrode target temperature by a preset downward margin in the event that the temperature of the insulative member reaches the predetermined insulation threshold temperature.

In a preferred arrangement, the temperature of the insulative member is repeatedly measured, and the electrode target temperature is adjusted by a preset downward margin each time that the temperature of the insulative member is at or above the predetermined insulation threshold temperature. Conveniently the electrode target temperature is adjusted by a preset upward margin each time that the temperature of the insulative member is below the predetermined insulation threshold temperature, until the electrode target temperature reaches its original predetermined value.

The invention will be further described below, by way of example only, with reference to the accompanying drawings.

BRIEF DESCRIPTION OF THE DRAWINGS

In the drawings:

FIGS. 5a and 5b are graphs of temperature against time, for a lesion generation device in accordance with the present invention.

DETAILED DESCRIPTION OF THE PREFERRED EMBODIMENT

Figure 1:
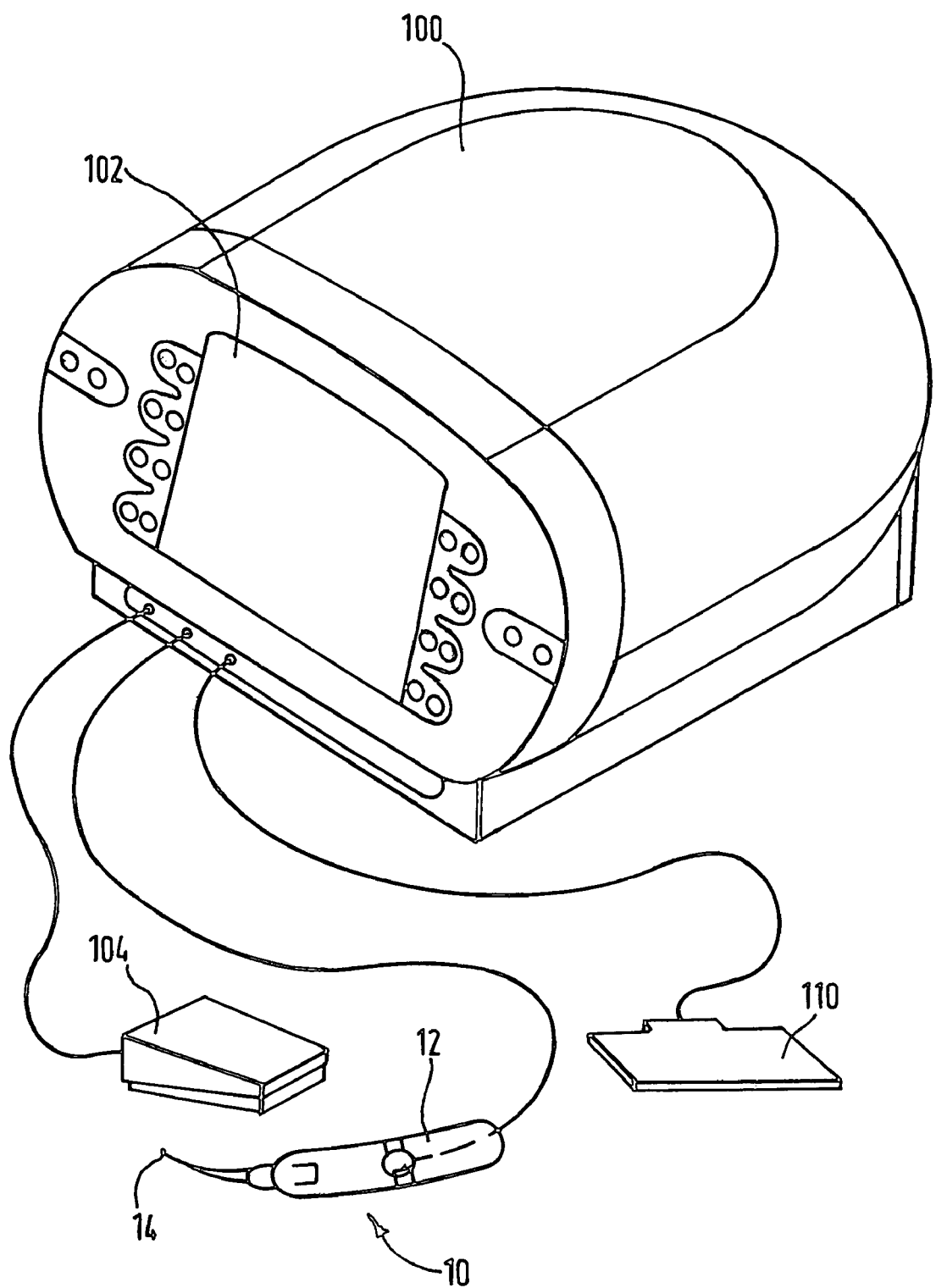
FIG. 1 is a schematic diagram of an electrosurgical system in accordance with the present invention.

FIG. 1 shows the apparatus for a typical embodiment of an RF electrosurgical device for forming lesions in body tissue. The system comprises a controller 100 (including an RF power supply) with a user input and display panel 102. Also provided are a foot switch 104, an electrical grounding pad 110 and a probe 10 including a surgical handpiece 12 with a surgical electrode 14. The user input allows the user to input different parameters to affect lesion size, including treatment duration, and total energy delivery.

The controller 100 converts the low frequency electrical energy supplied by a wall connection (not shown) into the high frequency or RF energy necessary for surgery. The user input and display panel 102 displays relevant parameters and provides buttons and switches for user input to the control systems. The foot switch 104 connected to the controller provides means for switching the unit on and off. The surgical handpiece 12 is also connected to the controller and is the means for delivering the RF energy to the surgical electrode 14. The electrical grounding pad 110 is also connected to the controller and floats at a reference electric potential. Other embodiments of this invention have no electrical grounding pad.

Figure 2:
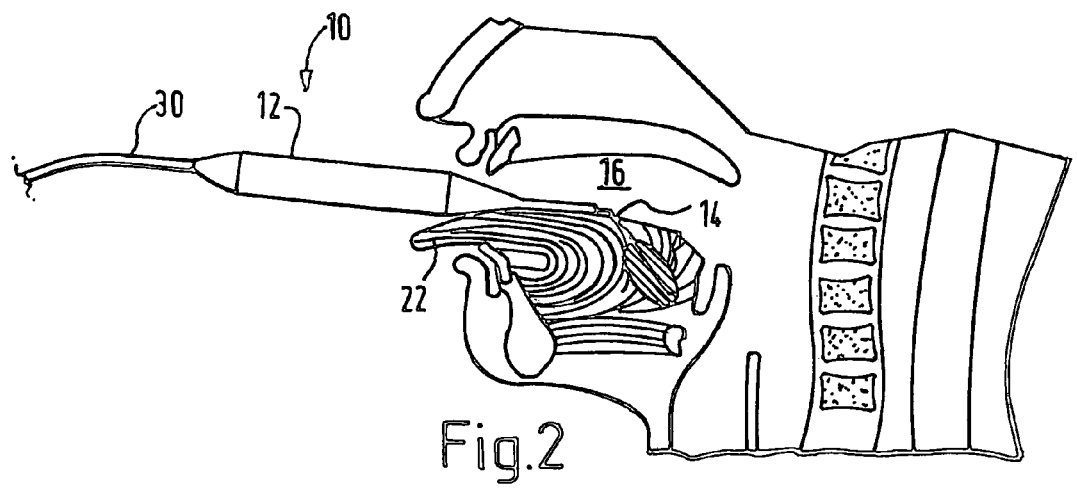
FIGS. 2 and 3 are schematic sectional views of a probe forming part of the system of FIG. 1, shown generating a lesion in the tongue of a patient.
Figure 3:
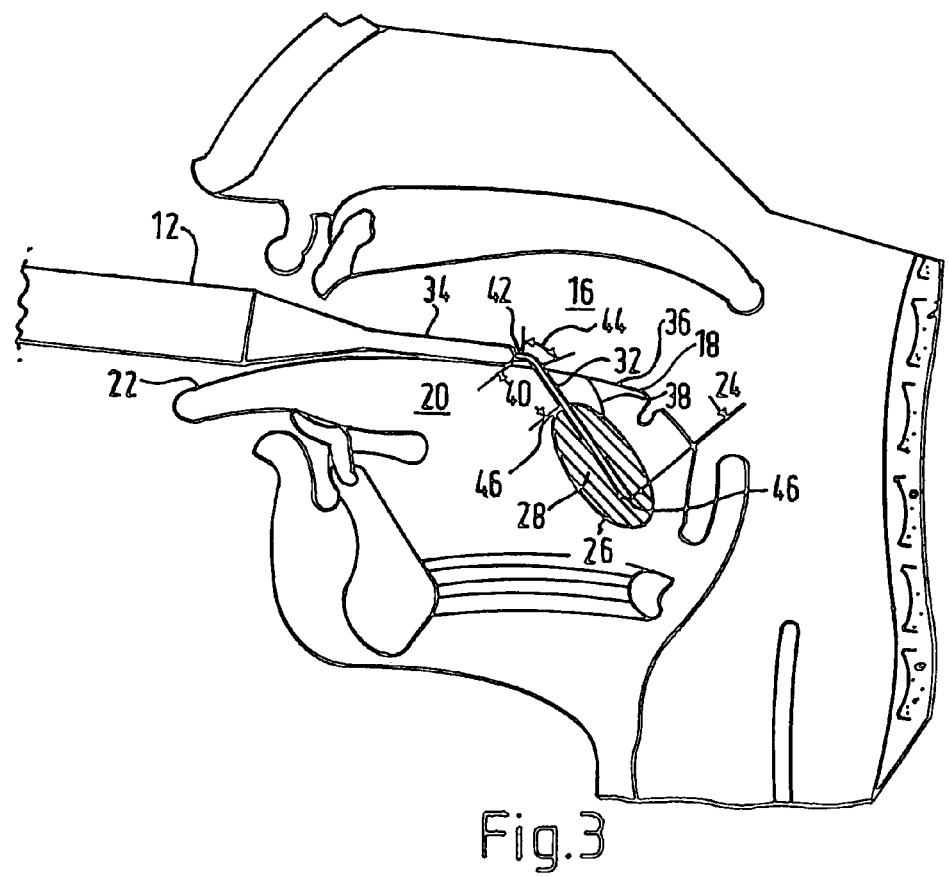

Referring now to FIGS. 2 and 3, the probe 10 is shown being used to reduce a volume of a selected site in an interior of a head and neck structure, and more particularly to a structure that is associated with an airway passage. Suitable anatomical structures include but are not limited to the tongue, uvula, soft palate tissue, tonsils, adenoids, turbinate structures and the like. In FIGS. 2 and 3, probe 10 is shown as including a handpiece 12 coupled to an electrode 14. Handpiece 12 can be a proximal portion of electrode 14 that is suitably configured to enable placement and removal of probe 10 to and from a selected anatomical structure and may include, in one embodiment, a proximal portion of electrode 14 that is insulated. Handpiece 12 and electrode 14 are sized and of a suitable geometry to be maneuverable in an oral cavity 16, pierce a tongue surface 18 and advance into an interior 20 of a tongue 22 a sufficient distance 24 to a tissue site 26. Electromagnetic energy is delivered to tissue site 26 to create cell necrosis at zone 28 without damaging a main branch of the hypoglossal nerve. A cable 30 is coupled to the electrode 14. For purposes of this disclosure, the main branches of the hypoglossal nerve are those branches which if damaged create an impairment, either partial or full, of speech or swallowing capabilities. Following the treatment, the treated structure of tongue 22 is repositioned in oral cavity 16. With this cell necrosis, the back of the tongue 22 moves in a forward direction away from the air passageway. The result is an increase in the cross-sectional diameter of the air passageway.

Handle 12 is preferably made of an electrically and thermally insulating-material. Electrode 14 can be made of a conductive material such as stainless steel. Additionally, electrode 14 can be made of a shaped memory metal, such as nickel titanium, commercially available from Raychem Corporation, Menlo Park, Calif. In one embodiment, only a distal end of electrode 14 is made of the shaped memory metal in order to effect a desired deflection.

Probe 10 can include visualization capability including but not limited to a viewing scope, an expanded eyepiece, fiber optics, video imaging, and the like.

Electrode 14 includes an insulator 32 which can be adjustable in length and in a surrounding relationship to an exterior surface of electrode 14. Insulator 32 serves as a barrier to thermal or RF energy flow. Insulator 32 can be in the form of a sleeve that may be adjustably positioned at the exterior of electrode 14. In one embodiment, the insulator can be made of a polyamide material and be a 0.002 inch (50 micron) shrink wrap. The polyamide insulating layer is semi-rigid.

Handpiece 12 can have a reduced diameter at a distal portion 34 to facilitate positioning, maneuverability, provide easier access to smaller openings and improve the visibility in the area where electrode 14 is to penetrate.

To use probe 10 in oral cavity 16, a topical and then a local anesthetic is applied to tongue 22. After a suitable period for the anesthesia to take effect, the physician may grasp the body of tongue 22 near the apex, using a gauze pad for a better grip. Tongue 22 is then drawn forward, bringing the body and the root of tongue 22 further forward for improved accessibility. Grasping handpiece 12, the physician positions a distal portion of electrode 14 at tongue surface 18. The position of electrode 14 in FIGS. 2 and 3, illustrates cell necrosis zone 28 below a mucosal surface 36 providing a protected zone 38. An insulated portion 40 of electrode 14 prevents delivery of energy to a main branch of a hypoglossal nerve and/or to mucosal surface 36.

Electrode 14 can have an angle 42 at a bend zone 44 which is lateral to a longitudinal axis of handpiece 12. Electrode 14 can be malleable to create different bend zones, depending on the anatomical structure and the insertion position of the anatomical structure. With the use of a bending fixture, not shown, the arc of angle 42 can be adjusted by the physician as needed at the time of treatment.

It will be appreciated that the term "electrode" in the specification generally means an energy delivery device. The device may be arranged to heat tissue using methods including but not limited to resistive heating, and heating by RF, microwave, or ultrasound energy. The preferred energy source is an RF source and electrode 14 is an RF electrode operated in either bipolar or monopolar mode with a ground pad electrode. In a monopolar mode of delivering RF energy, a single electrode 14 is used in combination with an indifferent electrode patch that is applied to the body to form the other contact and complete an electrical circuit. Bipolar operation is possible when two or more electrodes 14 are used. Multiple electrodes 14 may be used.

When the energy source is RF, an RF energy source may have multiple channels, delivering separately modulated power to each electrode 14. This separate modulation reduces preferential heating that occurs when more energy is delivered to a zone of greater conductivity and less heating occurs around electrodes 14 which are placed into less conductive tissue. If the tissue hydration or blood infusion in the tissue is uniform, a single channel RF energy source may be used to provide power for the treatment and cell necrosis zones are relatively uniform in size.

One or more sensors 46 are included and positioned at a distal end of electrode 14, and sensors 56 are positioned at the distal end of insulator 32. The sensors 46 and 56 are of conventional design, including but not limited to thermistors, thermocouples, resistive wires, and the like. A suitable sensor is a T type thermocouple with copper constantan, J type, E type, K type, fiber optics, resistive wires, thermocouple IR detectors, and the like.

Figure 4:
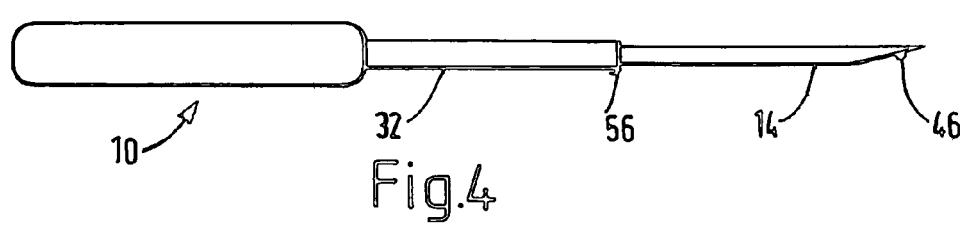
FIG. 4 is an enlarged side view of a distal end portion of the probe.

FIG. 4 is an enlarged view of the distal end of probe 10, showing electrode 14, insulator 32, electrode thermocouple 46, and insulation thermocouple 56. FIGS. 5a and 5b are shows a schematic graphs of the temperature profile of the device of FIG. 4, with the temperature detected by electrode thermocouple 46 being shown in FIG. 5a, and the temperature detected by insulator thermocouple 56 being shown in FIG. 5b. As shown in FIGS. 5a and 5b, when the probe is first energized, the electrode temperature rises quickly with the thermocouple 46 feeding back temperature readings to the controller 100, which compares the readings with a predetermined maximum electrode temperature $TE_{max}$, typically 110° C. The controller 100 compares the temperature detected by the thermocouple 46 with the maximum temperature, and also takes into account the rate of change of the detected temperature since the previous reading. The controller 100 adjusts the RF power delivered to the electrode 14 in accordance with these calculations. Readings are taken and adjustments are made on a repeated basis, typically every 60 ms. When the detected electrode temperature reaches $TE_{max}$, at time A as shown in FIG. 5a, the power of the RF energy supplied to the electrode is reduced so as to maintain the electrode temperature at the $TE_{max}$ level. U.S. Pat. No. 5,057,105 describes one such temperature control technique in more detail.

With the electrode temperature maintained at substantially 110° C., the temperature of the insulator 32 starts to rise, as shown in FIG. 5b. The controller 100 takes readings from the thermocouple 56, typically at a frequency of around 3 Hz, and is therefore able to detect when the insulation temperature reaches a threshold level $TI_{th}$, which is typically 62° C. This is shown as occurring at time B in FIG. 5b. Once the insulation temperature reaches $TI_{th}$, the controller reduces the target temperature of the electrode ($TE_{set}$) by a preset amount so that it is now less than $TE_{max}$. The target temperature is reduced by the preset amount (typically 0.5° C.) every time that the controller 100 interrogates the thermocouple 56, and the reading shows that the temperature is at or above the threshold level $TI_{th}$. Thus the electrode target temperature will be rapidly reduced from its previous level of 110° C., and the electrode temperature will correspondingly start to fall, causing a corresponding reduction in the insulation temperature. The insulation threshold $TI_{th}$ is set at a level such that, even if the insulation temperature continues to rise for a short while before it starts to fall, it will not reach an insulation temperature maximum level $TI_{max}$, at which tissue adjacent the insulator starts to be rendered non-viable.

The insulation temperature reduces as described above, until it once again falls below the threshold level $TI_{th}$. This situation is shown at C in FIGS. 5a and 5b, at which point the controller 100 starts to increase the electrode target temperature $TE_{set}$ by a similar preset amount for each interrogation of the thermocouple 56 that shows the insulator temperature to be below the threshold $TI_{th}$, until the target temperature once again reaches the maximum level of $TE_{max}$. This is shown as point D in FIG. 5a. This situation will continue until the insulator temperature once again reaches the threshold temperature (point E), or until the user proscribed treatment duration has elapsed, the required energy has been delivered, or until the footswitch is activated to switch off the RF signal and end the treatment process.

It has been found that the use of this insulation temperature control allows higher treatment temperatures to be used, while ensuring that tissue damage from insulator overheating is avoided. These higher temperatures have produced lesions comparable in size with those produced by the prior art devices, but with a greatly reduced treatment time and delivered energy. A typical prior art lesion generation device produces an acceptable lesion in around 4 to 5 minutes. The device of the present invention has been found to produce a lesion which is 70% of the size of the prior art lesion in only 60 seconds, and with only 40% of the delivered energy of the prior art system.

What is claimed is:

1. A method of forming a lesion in body tissue comprising:
providing a probe capable of contacting body tissue to be treated, the probe including at least one electrode and an insulative member covering at least a portion of the electrode;
delivering electromagnetic energy to the probe such as to raise the temperature of the tissue in contact with the probe;
measuring a temperature of the electrode;
comparing the temperature of the electrode with a predetermined electrode target temperature;
increasing the delivery of the electromagnetic energy until the electrode reaches the predetermined electrode target temperature;
controlling the delivery of the electromagnetic energy such that the electrode is maintained at the predetermined electrode target temperature;
measuring a temperature of the insulative member;
comparing the temperature of the insulative member with a predetermined insulation threshold temperature; and
adjusting the predetermined electrode target temperature by a preset downward margin when the temperature of the insulative member reaches the predetermined insulation threshold temperature.

2. The method of forming a lesion in body tissue according to claim 1, wherein the temperature of the insulative member is repeatedly measured, and the predetermined electrode target temperature is adjusted by the preset downward margin each time that the temperature of the insulative member is at or above the predetermined insulation threshold temperature.

3. The method of forming a lesion in body tissue according to claim 2, wherein the predetermined electrode target temperature is adjusted by a preset upward margin each time that the temperature of the insulative member is below the predetermined insulation threshold temperature, until the predetermined electrode target temperature reaches its original predetermined value.

4. The method according to claim 1, wherein the predetermined insulation threshold temperature is lower than a predetermined maximum temperature of the insulative member.

* * * * *